United States Patent
Warchocki et al.

(10) Patent No.: US 6,986,796 B2
(45) Date of Patent: *Jan. 17, 2006

(54) UNITARY LID FOR AN ELECTRICAL ENERGY STORAGE DEVICE

(75) Inventors: David Warchocki, North Tonawanda, NY (US); James Carroll, Buffalo, NY (US); Paul J. Quattrini, Amherst, NY (US); George McNamara, North Tonawanda, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 463 days.

This patent is subject to a terminal disclaimer.

(21) Appl. No.: 10/339,478

(22) Filed: Jan. 9, 2003

(65) Prior Publication Data

US 2004/0137319 A1    Jul. 15, 2004

Related U.S. Application Data

(63) Continuation-in-part of application No. 09/837,778, filed on Apr. 18, 2000, now abandoned.

(60) Provisional application No. 60/198,175, filed on Apr. 19, 2000.

(51) Int. Cl.
*H01M 6/00* (2006.01)
*H01M 2/08* (2006.01)
*H01M 2/02* (2006.01)

(52) U.S. Cl. .................. 29/623.1; 29/623.2; 429/175; 429/181

(58) Field of Classification Search ........... 429/175, 429/180, 181, 122; 29/623.1, 623.2; 205/663, 205/665
See application file for complete search history.

(56) References Cited

U.S. PATENT DOCUMENTS

| | | | |
|---|---|---|---|
| 347,440 A | 8/1886 | Partz | 429/178 |
| 393,395 A | 11/1888 | Roosevelt | 429/178 |
| 2,223,226 A | 11/1940 | Rieser | |
| 4,047,292 A | 9/1977 | Shaffer | |
| 4,455,357 A | 6/1984 | Rorer et al. | 429/179 |

(Continued)

FOREIGN PATENT DOCUMENTS

EP    1148562    * 10/2001

*Primary Examiner*—Patrick Joseph Ryan
*Assistant Examiner*—Thomas H. Parsons
(74) *Attorney, Agent, or Firm*—Michael F. Scalise

(57) ABSTRACT

A unitary lid for the casing of an electrochemical energy storage device is described. The lid has a terminal lead ferrule and a fillport formed from a single blank in a machining process. The lid does not require any welding except for securing it to the open end of a casing container. This helps the lid contribute to the cell's volumetric efficiency, which is especially important for cells powering implantable medical device.

26 Claims, 3 Drawing Sheets

U.S. PATENT DOCUMENTS

| | | | |
|---|---|---|---|
| 4,467,021 A | 8/1984 | Stocchiero | 429/175 |
| 4,695,519 A | 9/1987 | Rao et al. | 429/52 |
| 4,748,094 A | 5/1988 | Howard et al. | 429/90 |
| 5,104,755 A | 4/1992 | Taylor et al. | 429/181 |
| 5,173,375 A | 12/1992 | Cretzmeyer et al. | 429/72 |
| 5,209,994 A | 5/1993 | Blattenberger et al. | 429/213 |
| 5,306,581 A | 4/1994 | Taylor et al. | 429/181 |
| 5,439,760 A | 8/1995 | Howard et al. | 429/94 |
| 5,458,997 A | 10/1995 | Crespi et al. | 429/219 |
| 5,716,729 A | 2/1998 | Sunderland et al. | 429/66 |
| 5,750,286 A | 5/1998 | Paulot et al. | 429/211 |
| 5,798,906 A | 8/1998 | Ando et al. | 361/520 |
| 6,010,803 A * | 1/2000 | Heller et al. | 429/175 |
| 6,855,456 B2 * | 2/2005 | Taylor et al. | 429/181 |
| 2002/0132163 A1 | 9/2002 | Paulot et al. | |

* cited by examiner

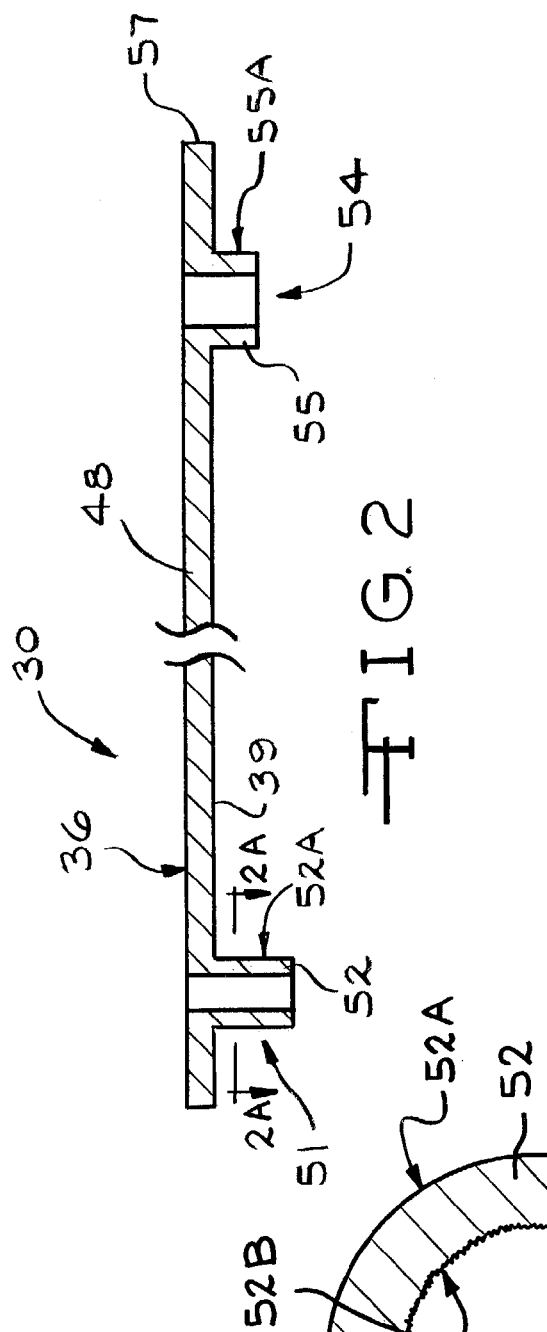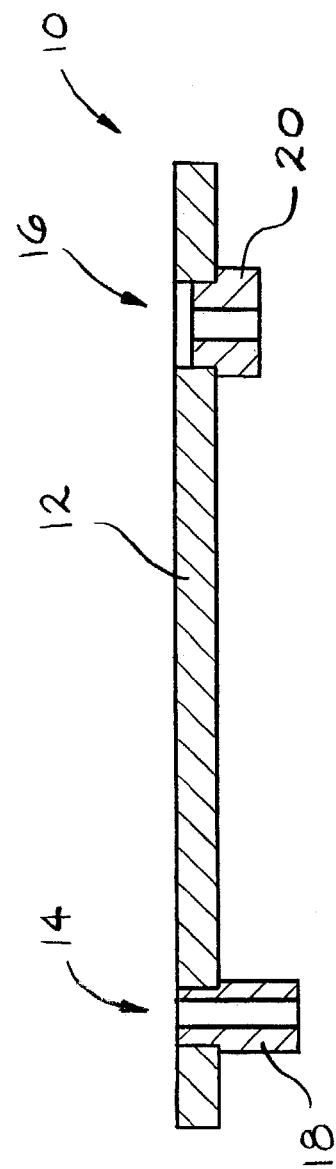

6,986,796 B2

UNITARY LID FOR AN ELECTRICAL ENERGY STORAGE DEVICE

CROSS-REFERENCE TO RELATED APPLICATIONS

This application is a continuation-in-part of U.S. application Ser. No. 09/837,778, filed Apr. 18, 2001, now abandoned, which claims priority on U.S. provisional application Ser. No. 60/198,175, filed Apr. 19, 2000.

FIELD OF INVENTION

The present invention relates to electrical energy storage devices, such as electrochemical cells and capacitors. More particularly, the present invention relates to lids or covers for casings housing electrical energy storage devices.

BACKGROUND OF THE INVENTION

Electrochemical cells and capacitors typically include a container with an opening that is closed by a lid or cover welded to the container to form a casing for the electrical energy storage device. Inside the container is an anode/cathode electrode assembly activated by an electrolyte. The container and the lid are of electrically conductive material and serve as a contact for either the anode electrode or the cathode electrode. In a case negative cell, the anode current collector is in contact with the casing while for a case positive design, the opposite is true. The other of the anode electrode and the cathode electrode not in contact with the casing is connected to a terminal lead electrically insulated from the casing by a glass-to-metal seal. When a load is connected to the casing and the terminal pin in an electrochemical cell, a chemical reaction in the cell results in a voltage differential that generates an electrical current to power the load, for example, a medical device.

The lid must provide access to the interior of the casing for at least two purposes. First, the terminal lead connected to the anode or the cathode current collector must pass through one of the lid openings to a position exterior of the casing. Second, the electrolyte must be filled into the housing through the other lid opening. Conventionally, two openings are defined in the lid for this purpose. The openings usually have structures connected to the lid to aid in sealing them. For example, a terminal lead ferrule is attached to the lid to accommodate the electrical lead and a fillport/closure assembly is used for sealing the fill opening.

FIG. 1 shows an exemplary prior art construction where the lid 10 is formed of a generally rectangular blank 12 stamped from a sheet of electrically conductive material. During stamping, two openings 14, 16 are provided through the blank 12. A terminal lead ferrule 18 and a fillport 20 are sleeve-shaped members formed of discrete parts that are welded to the blank 12, each in registration with one of the openings 14, 16.

This prior art lid requires a number of manufacturing, inspection, and assembly steps due to the use of at least three discrete parts, i.e. the blank 12, the terminal lead ferrule 18 and the fillport 20. Specifically, the blank 12 is punched from a sheet of metal using a fine blanking or stamping operation. Simultaneously, the two openings 14, 16 are punched through the blank 12. The lid 10 goes through an annealing process, a passivation process (e.g. removal of free iron from the surface of the part) and a cleaning process before it is inspected. The discrete terminal lead ferrule 18 and the discrete fillport 20 go through the same process steps prior to attachment to the blank 12. The terminal lead ferrule 18 and the fillport 20 are then positioned in registration with the openings 14, 16 and welded thereto. These welds are vulnerable to variations in quality and each must be inspected. As those who are skilled in the art will readily recognize, these manufacturing, assembly, and inspection steps require time and labor. Also, inventory of the parts must be tracked and maintained, further adding to the cost of an electrical energy storage device.

Another problem with the prior art cover construction is that crevice corrosion can occur where the terminal lead ferrule 18 and the fillport 20 are secured to the openings 14, 16 in the lid 10. Typically, the terminal lead ferrule 18 and the fillport 20 are inserted from the bottom or interior surface of the blank 12 before being welded. This welding may leave cracks or crevices between the mating surfaces leading to entrapment of materials such as cleaning solutions. As such, corrosion can occur around these crevices.

One prior art lid or cover for an electrochemical cell is described in U.S. Pat. No. 6,010,803 to Heller, Jr. et al. This lid is formed by a metal injection molding process which requires that the intersections between the terminal lead ferrule and the main body of the lid and between the fillport structure and the lid be slightly curved or "radiused." Heller, Jr. et al. believes that radiused junctions facilitate the flow of material during the metal injection molding process. This eliminates areas of stress concentration that can cause the molded material to crack.

There are several problems with the Heller, Jr. et al. metal injection-molded lid. First, the radiused areas detract from the internal volume available to active and other no-active cell components. Electrical energy storage devices of the present invention are used in implantable medical devices such as cochlear implants. These are extremely small devices that require extremely compact power sources where maximizing internal volume is important.

Secondly, a machined lid according to the present invention has a higher density and, consequently, less porosity than the metal injection molded lid. Metal injection molded materials require a binder, and even though technology advances have reduced the amount of binder required, metal density is still about 98% to about 98.5%, after curing. In contrast, a one piece lid according to the present invention machined from bar or rod stock has a density of about 99.99%, and maintains acceptable mechanical properties required for glassing the terminal lead in the glass-to-metal seal.

Lastly, design structures can be repositioned or changed to accommodate a particular electrical energy storage device. Typically, this requires a program change to offset features, change tolerances or add new features. In contrast, metal injection molded components require a whole new set of tooling which is capitol intensive.

U.S. Pat. No. 5,173,375 to Cretzmeyer et al. related to a unitary lid for closing a casing for an electrochemical cell. This prior art lid is stamped from a metal blank. The problem is that the stamping process introduces minute stress fracture into the product lid. These are sights of potential seal failure and corrosion.

Accordingly, what is needed is a unitary lid having a terminal ferrule and fillport structure that reduces the manufacturing, assembly, and inspection steps described above and is as compact in size as possible.

SUMMARY OF THE INVENTION

The present invention meets the above-described needs by providing a unitary lid including a terminal ferrule and a fillport structure formed from a single blank of conductive material. A starting blank is provided with a thickness sufficient to meet the design features for a particular electrical energy storage device. The terminal ferrule and fillport are then created in the blank via a machining process such that the junctions where both the terminal lead ferrule and the fillport structure meet with the under side of the lid are at right angles. The process of the present invention eliminates the need for welding of the sleeve-shaped terminal lead ferrule and fillport, and requires fewer handling operations while optimizing the cell's internal volume.

These and other aspects of the present invention will become increasingly more apparent to those skilled in the art by reference to the following description and the appended drawings.

BRIEF DESCRIPTION OF THE DRAWINGS

The invention is illustrated in the drawings in which like reference characters designate the same or similar parts throughout the figures of which:

FIG. 1 is cross-sectional side elevation view of a conventional lid with a welded terminal lead ferrule and fillport structure.

FIG. 2 is a cross-sectional side elevation view of the unitary lid of the present invention.

FIG. 2A is a cross-sectional view taken along line 2—2 of FIG. 2.

DETAILED DESCRIPTION OF THE EMBODIMENTS

Figure 3:
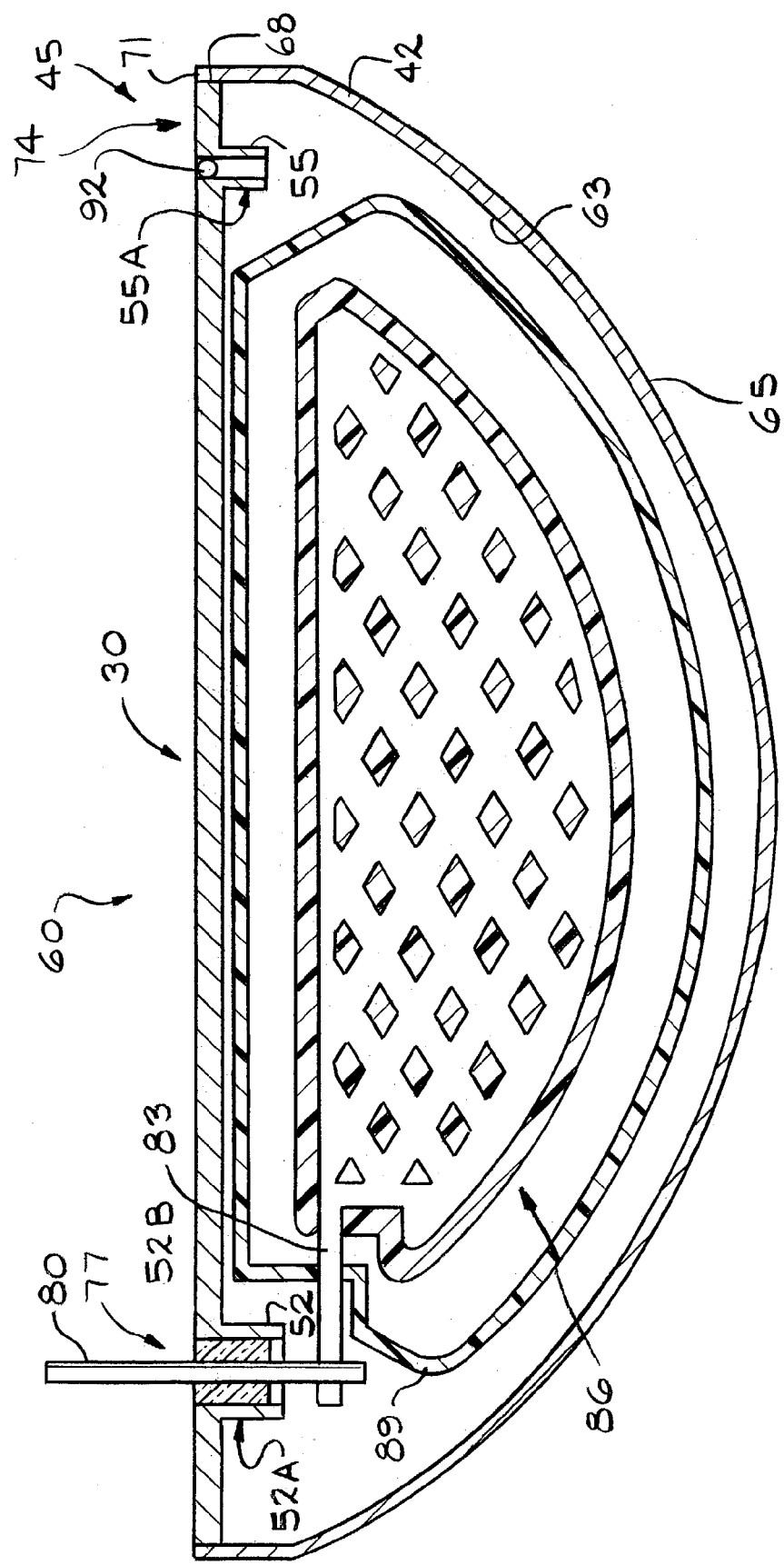
FIG. 3 is a cross-sectional side elevation view of an exemplary electrochemical cell with the unitary lid of the present invention attached to a container to provide a casing for the electrode assembly.

Throughout this description the terms "lid" and "cover" are used interchangeably to refer to the member shown in FIG. 2 that is attached to the open end of a container or housing to form a casing for an electrical energy storage device.

Electrochemical cells or batteries generate electrical current from chemical energy. Capacitors are used to store relatively large quantities of electrical energy for subsequent discharge. Often, these types of electrical energy storage devices are used in medical devices such as heart pacemakers, cardiac defibrillators, neurostimulators, cochlear implants, and the like. In that light, the lid of the present invention is a compact unitary member with space saving right angle surfaces at the junction of the lid body and both the terminal ferrule and the fillport. As will be described hereinafter, this makes the present lid particularly applicable for electrical energy storage devices intended for incorporation into implantable medical devices.

Turning now to the drawings, FIG. 2 shows a unitary lid or cover 30 according to the present invention formed by machining a rectangular blank (now shown) of an electrically conductive material such as stainless steel, titanium, nickel, aluminum, and the like. Lid 30 has generally opposing major planar upper and lower surfaces 36 and 39. When in place closing the open end of the container 42 of a casing 45 (FIG. 3), upper surface 36 is an exterior surface and inner surface 39 is an interior surface. Lid 30 is formed of generally three portions or regions: a main body portion 48 having the opposed upper and lower surfaces 36, 39, a terminal ferrule portion 51, and a fillport portion 54. The terminal lead ferrule 51 and fillport portion 54 are completely integral or unitary with main body portion 48. As used herein, completely integral means being of a single continuous body of material. In other words, by machining the lid 30 from a suitable blank, the terminal ferrule 51 and the fillport portion 54 are not separate or discrete parts, but rather are completely unitary with the main body portion 48 forming a single part.

Lid 30 terminates along a peripheral edge 57 that is generally perpendicular to the planar upper and lower lid surfaces 36, 39. In the embodiment shown, main body portion 48 is generally rectangular in peripheral shape. The terminal ferrule 51 is a sleeve-shaped portion having a surrounding side wall 52 with a cylindrical outer surface 52A. The cylindrically shaped inner surface 52B of the surrounding side wall has a machined roughened texture. In other words, the inner surface 52B is not threaded, but is roughened by the action of a rotating machining bit removing material from the blank to form the cylindrically shaped opening. The machined roughness enhances the integrity of the glass-to-metal seal by providing scoring marks that serve as attachment structures for the glass to fill and anchor into. With a prior art metal injection molded lid according to the previously discussed U.S. Pat. No. 6,010,803 to Heller, Jr. et al. or a metal stamped lid according to U.S. Pat. No. 5,173,375 to Cretzmeyer et al., there is no such surface roughness to which the glass can anchor. Also, the hoop strength of a lid produced by a metal injection molding process is reduced due to the extended curing time required.

The cylindrical outer surface 52A of the ferrule side wall 52 meets the lower surface 39 of the lid main body portion 48 at a right angle or a normal orientation. Similarly, the fillport 54 is a sleeve-shaped portion having a cylindrically shaped opening provided by a surrounding side wall 55. The cylindrical outer surface 55A of the fillport side wall 55 meets the lower surface of the lid main body portion 48 at a right angle.

While the upper ends of the terminal ferrule 51 and the fillport 54 are shown co-planar with the upper surface 36 of the lid 30, the present invention should not be so limited. In that respect, these structures can extend above the upper lid surface 36. What is important is that they are unitary with the main body portion 48.

It will be understood by those of ordinary skill in the art that the main body portion 48 of the lid 30 may be of any suitable shape to mate with and close an opening in a container 42 for a casing, which also may be of any suitable shape. Therefore, the present invention contemplates any configuration of two portions of an electrical energy storage device casing which when mated form a cavity therein. This includes casing of a cylindrical shape, prismatic shape, button shape and casing formed of mating portions, such as described in U.S. application Ser. No. 09/757,232, filed Jan. 9, 2001. This application is assigned to the assignee of the present invention and incorporated herein by reference.

Either one of such portions of the casing, i.e., the lid or the container, or either one of the mating portions, may include the terminal ferrule portion 51 and the fillport portion 54 and be formed as a single part. What is important is that the respective outer surfaces 52A, 55A of the terminal ferrule 52 and the fillport 55 meet the lower or inner surface 39 of the lid main body portion 48 at a normal orientation. This means that as little internal casing volume as possible is occupied by the unitary lid 30. Such a construction benefits volumetric cell efficiency, which is especially important in electrical energy storage devices intended for incorporation in implantable medical devices.

FIG. 3 shows an illustrative exemplary electrochemical cell 60 incorporating a lid or cover according to the present invention. The exemplary cell 60 is described in U.S. Pat. No. 5,750,286 to Paulot et al., which is assigned to the assignee of the present invention and incorporated herein by reference. The cell 60 includes the casing 45 made of metal, such as stainless steel, titanium, nickel, aluminum, or other suitable electrically conductive material. Casing 45 is formed of two portions: the container shell 42 and the lid 30. Container 42 has an interior surface 63 and an opposite exterior surface 65. Further, container 45 terminates in a peripheral region 68 at a peripheral edge or rim 71. Peripheral region 68 defines an open side or opening 74 leading into the container 42. Accordingly, the container 42 forms generally all but one open side of casing 45. Lid 30 closes opening 74 and is attached to the peripheral region 68, such as by welding.

As shown in FIG. 3, the terminal ferrule 52 supports a glass-to-metal seal 77 for a terminal lead 80 connected to the current collector 83 of one of the electrodes, for example the cathode electrode 86. The anode (not shown) is segregated from the cathode by a separator 89. The anode/cathode electrode assembly is then activated by an electrolyte (not shown) filled in the casing, and sealed therein by a closure means, such as ball 92 sealed in the fillport portion 54. Those skilled in the art will understand that the present invention is not limited to any particular closure structure.

In accordance with the previous description, it will be evident that the present invention is applicable to any type of electrical energy storage device in which a housing is used that has a container portion with an open side and a cover for closing the container, thereby forming a casing for the storage device. In that respect, the present invention is applicable to low rate, medium rate, high rate, case negative and case positive electrochemical cells of both primary and secondary chemistries. Examples of such cells include lithium iodine cells, lithium thionychloride cells, lithium silver vanadium oxide cells, lithium carbon monofluoride cells, lithium manganese dioxide cells, and secondary cells containing lithium cobalt oxide, and the like.

It will further be recognized that such cells may take one of various configurations. For example, depending on the type of cell, the configuration of the anodes, cathodes, terminal lead ferrule portions, fillports, etc. will vary. Also, for example, depending on the cell, the materials housed in the casing will vary. Such materials may take the form of a liquid or a solid depending on the type of cell. Therefore, it should be clear that the present invention is in no manner limited to the illustrative cell described herein and is applicable to all types of electrochemical chemistries.

The present invention is also applicable to capacitors, such as those described in U.S. Pat. Nos. 5,926,362 and 6,334,879, both to Muffoletto et al. These patents are assigned to the assignee of the present invention and incorporated herein by reference.

Figure 5:
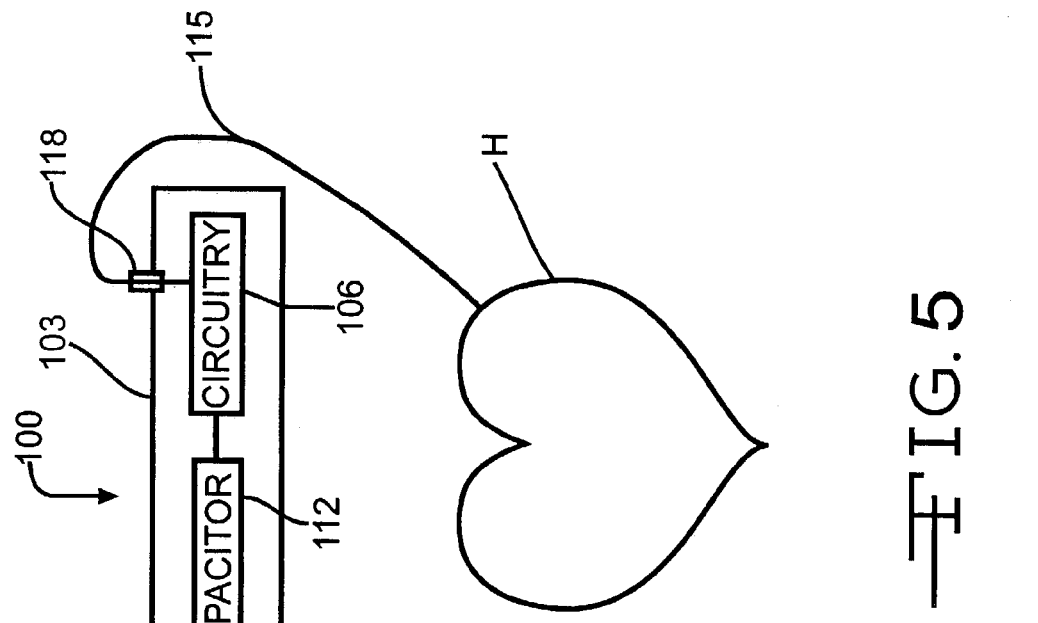
FIG. 5 is an enlarged schematic of the indicated area in FIG. 4 particularly showing the control circuitry 106, the electrochemical cell 109 and capacitor for the medical device 100 connected to the patient's heart H.
Figure 4:
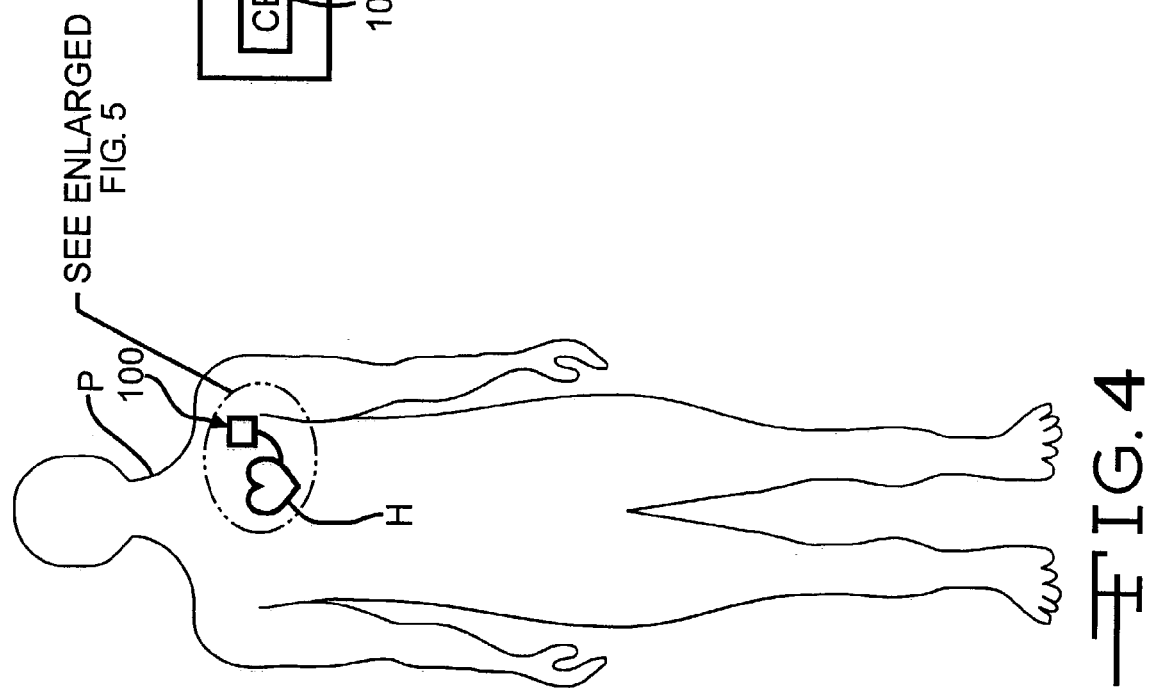
FIG. 4 is a schematic of a patient P provided with an implantable medical device 100.

FIGS. 4 and 5 show a patient P having a medical device 100, such as an implantable cardiac defibrillator, implanted inside the body. The enlarged schematic shows the medical device 100 comprising a housing 103 containing control circuitry 106 powered by an electrochemical cell 109. The cell 109 is also connected to a capacitor 112. The control circuitry 106 is connected to at least one conductor 115 by a hermetic feedthrough 118, as is well known by those skilled in the art. The distal end of the conductor connects to the heart H for delivering a therapy thereto from the capacitor 112 charged by the cell 109. The cell 109 and capacitor 112 are both built having a unitary lid 30 closing their casings according to the present invention.

Periodically, the patient will go to a medical facility, and the like, where the deliverable capacity determined by the control circuitry 106 is read to determine if the cell has discharged to the point that it is approaching its end-of-life, typically at an open circuit voltage of about 2.0 volts. If so, this indicates that it is time for the physician to schedule the patient for surgery to replace the medical device with a new one.

It is appreciated that various modifications to the inventive concepts described herein may be apparent to those of ordinary skill in the art without departing from the spirit and scope of the present invention as defined by the appended claims.

What is claimed is:

1. An electrical energy storage device, which comprises:
   a) a container having a surrounding side wall providing an opening leading into the container;
   b) an electrode assembly comprising an anode and a cathode in an electrochemical association with each other and disposed inside the container;
   c) a lid having space apart upper and lower surfaces joined by a peripheral edge and secured to the open end of the container to provide a casing housing the electrode assembly, wherein the lid has at least a unitary terminal ferrule extending below the lid lower surface and comprising a cylindrically shaped inner surface with at least a portion thereof having machined scoring marks;
   d) a terminal lead connected to one of the anode and cathode electrodes and extending through the terminal ferrule to a position spaced above the upper surface of the lid, wherein a glass surrounds the terminal lead and fills and anchors into the machined scoring marks to hermetically seal the terminal lead in the terminal ferrule in an insulated relationship with respect to the casing; and
   e) an electrolyte provided in the casing to activate the anode and cathode electrodes.

2. The electrical energy storage device of claim 1 wherein an outer surface of the terminal ferrule is in a normal orientation with respect to the lid, lower surface.

3. The electrical energy storage device of claim 1 wherein an outer surface of the terminal ferrule is cylindrical.

4. The electrical energy storage device of claim 1 wherein the machined scoring marks on the inner surface of the terminal ferrule are characterized as having been provided by a rotating machining bit.

5. The electrical energy storage device of claim 1 wherein the lid has a unitary fill port extending below the lid lower surface.

6. The electrical energy storage device of claim 5 wherein an outer surface of the fill port is in a normal orientation with the lower lid surface.

7. The electrical energy storage device of claim 5 wherein an outer surface of the fillport is cylindrical.

8. The electrical energy storage device of claim 1 wherein the lid is of a conductive material.

9. The electrical energy storage device of claim 8 wherein the conductive material is selected from the group consisting of stainless steel, titanium, nickel, and aluminum.

10. The electrical energy storage device of claim 1 as either an electrochemical cell or a capacitor.

11. A lid for closing an open end of a casing for an electrochemical energy storage device, the improvement in the lid comprising:

spaced apart upper and lower surfaces joined by a peripheral edge, wherein the lid has at least a unitary terminal ferrule extending below the lid lower surface and comprising a cylindrically shaped inner surface with at least a portion thereof having machined scoring marks.

12. The lid of claim 11 wherein the machined scoring marks on the inner surface of the terminal ferrule are characterized as having been provided by a rotating machining bit.

13. The lid of claim 11 wherein the lid has a unitary fill port extending below the lid lower surface.

14. An implantable medical device, which comprises:
   a) a device container;
   b) a control circuitry; and
   c) an electrical energy storage device, wherein the control circuitry and the electrical energy storage device are housed in the device container, the electrical energy storage device comprising:
      i) a container having a surrounding side wall providing an opening leading into the container;
      ii) an electrode assembly comprising an anode and a cathode in an electrochemical association with each other and disposed inside the container;
      iii) a lid having space apart upper and lower surfaces joined by a peripheral edge and secured to the open end of the container to provide a casing housing the electrode assembly, wherein the lid has at least a unitary terminal ferrule extending below the lid lower surface and comprising a cylindrically shaped inner surface with at least a portion thereof having machined scoring marks;
      iv) a terminal lead connected to one of the anode and cathode electrodes and extending through the terminal ferrule to a position spaced above the upper surface of the lid, wherein a glass surrounds the terminal lead and fills and anchors into the machined scoring marks to hermetically seal the terminal lead in the terminal ferrule in an insulated relationship with respect to the casing; and
      v) an electrolyte provided in the casing to activate the anode and cathode electrodes.

15. A method for providing a lid for a casing of an electrochemical energy storage device, comprising the steps of:
   a) obtaining a blank; and
   b) machining the blank to provide the lid having spaced apart upper and lower surfaces joined by a peripheral edge, and a unitary terminal ferrule extending below the lid lower surface and comprising a cylindrically shaped inner surface with at least a portion thereof having machined scoring marks.

16. The method of claim 15 including providing an outer surface of the terminal ferrule in a normal orientation with the lid lower surface.

17. The method of claim 15 including providing an outer surface of the terminal ferrule being cylindrical.

18. The method of claim 15 including providing the lid having a unitary fillport extending below the lid lower surface.

19. The method of claim 18 including providing an outer surface of the fillport being in a normal orientation with respect to the lid lower surface.

20. The method of claim 15 including providing the terminal ferrule having the machined scoring marks on the inner surface provided by a rotating machining bit.

21. The method of claim 15 including providing the lid of a conductive material.

22. A method for providing an electrical energy storage device, comprising the step of:
   a) providing a container having a surrounding side wall with an opening leading into the container;
   b) disposing an electrode assembly comprising an anode and a cathode in an electrochemical association with each other inside the container;
   c) machining a blank to provide a lid having spaced apart upper and lower surfaces joined by a peripheral edge and at least a unitary terminal ferrule extending below the lid lower surface and comprising a cylindrically shaped inner surface with at least a portion thereof having machined scoring marks, wherein an outer surface of the terminal ferrule is in a normal orientation with the lid lower surface;
   d) hermetically sealing a terminal lead in the terminal ferrule in an insulated relationship with respect to the lid by a glass surrounding the terminal lead filling and anchoring into the machined scoring marks;
   e) connecting the terminal lead to one of the anode and cathode electrodes;
   f) securing the lid to the container to close the opening leading therein and thereby providing a casing for the electrical energy storage device with the terminal lead extending through the terminal ferrule to a position spaced above the upper surface of the lid; and
   g) activating the anode and cathode electrodes with an electrolyte provided in the casing.

23. The method of claim 22 including providing the outer surface of the terminal ferrule being cylindrical.

24. The method of claim 22 including machining the blank having a unitary fillport extending below the lid lower surface.

25. The method of claim 22 including providing an outer surface of the fillport being in a normal orientation with the lid lower surface.

26. The method of claim 22 including providing an outer surface of the fillport being cylindrical.

* * * * *